United States Patent
Belski et al.

(10) Patent No.: US 11,408,876 B2
(45) Date of Patent: Aug. 9, 2022

(54) MODULAR GAS MONITORING SYSTEM

(71) Applicant: Industrial Scientific Corporation, Pittsburgh, PA (US)

(72) Inventors: Timothy J. Belski, Washington, PA (US); Rodney David Brenstuhl, Amsterdam, OH (US); Joshua Allen Futrell, Pittsburgh, PA (US); Charles Dennis Hughes, Moon Township, PA (US); Thomas Michael Mikulin, New Wilmington, PA (US); Henry J. Suwalski, Cranberry Township, PA (US); Daniel James Timco, McDonald, PA (US)

(73) Assignee: Industrial Scientific Corporation, Pittsburgh, PA (US)

( * ) Notice: Subject to any disclaimer, the term of this patent is extended or adjusted under 35 U.S.C. 154(b) by 0 days.

(21) Appl. No.: 16/411,465

(22) Filed: May 14, 2019

(65) Prior Publication Data
US 2019/0265217 A1     Aug. 29, 2019

Related U.S. Application Data

(63) Continuation of application No. 14/996,482, filed on Jan. 15, 2016, now Pat. No. 10,324,073.

(51) Int. Cl.
*G01N 33/00* (2006.01)
*G08B 25/14* (2006.01)
(Continued)

(52) U.S. Cl.
CPC ..... *G01N 33/0073* (2013.01); *G01N 33/0063* (2013.01); *G08B 13/19684* (2013.01);
(Continued)

(58) Field of Classification Search
CPC ........... G01N 33/0073; G01N 33/0063; G08B 21/12; G08B 25/14
See application file for complete search history.

(56) References Cited

U.S. PATENT DOCUMENTS

| 4,173,886 A | 11/1979 | Archbold et al. |
| 4,992,738 A * | 2/1991 | May .................. G01N 33/0054 |
| | | 205/779.5 |

(Continued)

FOREIGN PATENT DOCUMENTS

| CN | 200989234 Y | 12/2007 |
| CN | 101964890 A | 2/2011 |

(Continued)

OTHER PUBLICATIONS

"Drager", http://www.draeger.com/sites/en_uk/Pages/Chemical-Industry/Draeger-X-zone-5000.aspx, p. 1.
(Continued)

*Primary Examiner* — Patricia D Valenzuela
(74) *Attorney, Agent, or Firm* — GTC Law Group PC & Affiliates (57) ABSTRACT

A monitoring system may include a module configured to couple to a base. The module may include a memory configured to store a firmware application and data, a processor operably coupled to the memory and configured to execute firmware to control the monitoring system, a wireless communication transceiver configured to allow communications between the module and other modules external to the monitoring system, and at least one sensor. The monitoring system is operable to monitor data measured via the at least one sensor and provide monitoring and alarm functions. The module is replaceable separately from the base, which has a shape generally resembling a safety cone.

17 Claims, 8 Drawing Sheets

Related U.S. Application Data (60) Provisional application No. 62/104,194, filed on Jan. 16, 2015.

(51) Int. Cl.
  *G08B 21/12* (2006.01)
  *H04N 5/232* (2006.01)
  *G08B 13/196* (2006.01)

(52) U.S. Cl.
  CPC .............. *G08B 21/12* (2013.01); *G08B 25/14* (2013.01); *H04N 5/23216* (2013.01)

(56) References Cited

U.S. PATENT DOCUMENTS

| | | | |
|---|---|---|---|
| D409,507 S | 5/1999 | Ishii | |
| 6,182,497 B1 | 2/2001 | Krajci | |
| D450,254 S | 11/2001 | Ishii | |
| 6,442,639 B1 | 8/2002 | McElhattan et al. | |
| 6,679,094 B2 | 1/2004 | Wang et al. | |
| D494,074 S | 8/2004 | Ishii | |
| D526,223 S | 8/2006 | Ishii et al. | |
| D527,293 S | 8/2006 | Ishii | |
| D531,921 S | 11/2006 | Banba | |
| D532,325 S | 11/2006 | Tokuda et al. | |
| 7,286,894 B1 | 10/2007 | Grant et al. | |
| 7,336,191 B2 | 2/2008 | Drews et al. | |
| D563,247 S | 3/2008 | Ishii | |
| 7,861,424 B2 | 1/2011 | Munroe et al. | |
| D684,068 S | 6/2013 | Ishii | |
| D723,398 S | 3/2015 | Ishii | |
| D766,753 S | 9/2016 | Ishii et al. | |
| D766,754 S | 9/2016 | Aoki et al. | |
| 9,514,632 B2 | 12/2016 | Hunter et al. | |
| D777,588 S | 1/2017 | Aoki et al. | |
| D781,730 S | 3/2017 | Ishii et al. | |
| D781,731 S | 3/2017 | Ishii | |
| 9,613,521 B2 | 4/2017 | Hunter et al. | |
| 10,324,073 B2 | 6/2019 | Belski et al. | |
| 2005/0000271 A1 | 1/2005 | Rabenecker et al. | |
| 2007/0063828 A1 | 3/2007 | Drews et al. | |
| 2007/0241911 A1* | 10/2007 | Swan | G08B 21/0208 340/573.1 |
| 2007/0279002 A1* | 12/2007 | Partovi | H02J 7/0027 320/115 |
| 2008/0256445 A1* | 10/2008 | Olch | G16H 40/67 715/700 |
| 2009/0056408 A1* | 3/2009 | Tryfonos | G05D 16/04 73/1.06 |
| 2011/0313555 A1* | 12/2011 | Shoham | G08B 21/0208 700/94 |
| 2013/0169735 A1* | 7/2013 | Barker | G08B 21/0277 348/14.02 |
| 2014/0216129 A1 | 8/2014 | Schmidlin et al. | |
| 2014/0232555 A1 | 8/2014 | Aakvaag et al. | |
| 2014/0253024 A1 | 9/2014 | Rautiainen et al. | |
| 2014/0257127 A1* | 9/2014 | Smith | A61B 5/082 600/532 |
| 2014/0361901 A1* | 12/2014 | Hoefer | G08B 17/00 340/628 |
| 2015/0206421 A1* | 7/2015 | Moffa | G08B 25/14 340/514 |
| 2016/0189520 A1* | 6/2016 | Papageorge | G01N 33/0036 340/632 |
| 2016/0209386 A1 | 7/2016 | Belski et al. | |

FOREIGN PATENT DOCUMENTS

| | | |
|---|---|---|
| CN | 102426764 B | 11/2013 |
| CN | 203596089 U | 5/2014 |
| CN | 203721201 U | 7/2014 |
| CN | 107110746 A | 8/2017 |
| CN | ZL201630325230.5 | 10/2017 |
| JP | 2006085430 A | 3/2006 |
| JP | 2008033756 A | 2/2008 |
| JP | 2014524180 A | 9/2014 |
| JP | 1575214 S | 6/2016 |
| JP | 1566522 S | 12/2016 |
| JP | 2018504706 A | 2/2018 |
| WO | 0114873 A1 | 3/2001 |
| WO | 0182063 A1 | 11/2001 |
| WO | 2016115438 A1 | 7/2016 |

OTHER PUBLICATIONS

"Radius BZ1", availalbe from internet, <URL: http://www.indsci.com/products/area monitors/radius/>, 4 pages.

"Radius BZ1 Overview", available from internet, <URL: https://www.youtube.com/watch?v=t34Ja8aCimU>, 1 page.

16737947.8, "European Application Serial No. 16737947.8, Extended European Search Report dated Sep. 11, 2018", Industrial Scientific Corporation, 9 pages.

PCT/US2016/013558, "International Application Serial No. PCT/US2016/013558, International Preliminary Report on Patentability and Written Opinion dated Jul. 27, 2017", Industrial Scientific Corporation, 8 Pages.

PCT/US2016/013558, "International Application Serial No. PCT/US2016/013558, International Search Report and Written Opinion dated May 3, 2016", Industrial Scientific Corporation, 14 pages.

U.S. Appl. No. 29/551,639, filed Jan. 15, 2016, Pending.
U.S. Appl. No. 29/723,232, filed Feb. 5 2020, Pending.
U.S. Appl. No. 29/723,236, filed Feb. 5, 2020, Pending.

* cited by examiner

MODULAR GAS MONITORING SYSTEM

CROSS-REFERENCE TO RELATED APPLICATIONS

This application is a continuation of U.S. patent application Ser. No. 14/996,482, filed Jan. 15, 2016 (ISCI-0023-U01 and entitled Modular Gas Monitoring System," which claims the benefit of U.S. Provisional Application No. 62/104,194, filed Jan. 16, 2015 and entitled "Modular Gas Monitoring System."

All of the above applications are incorporated by reference in their entirety as if fully set forth herein.

BACKGROUND

Gas monitoring devices are used in industrial work environments where individuals may be at risk of exposure to a number of hazardous substances and environmental conditions, such as toxic gases, highly combustible gases, and oxygen-depleted environments. Typical gas monitoring devices often include one or more gas sensors, a processing component and firmware to analyze the gas sensor information, a display to present gas detection information to a user, and alarms to alert the user to any hazardous conditions and/or device status. In addition, the gas monitoring devices may include bump testing and calibration functionality to ensure they are calibrated and performing properly.

Gas monitoring devices are life-critical equipment in many industrial environments. Accordingly, manufacturers are continually developing improved components and firmware that are, for example, more efficient, more accurate, more sensitive, or longer lasting. However, it is often difficult and/or cost-prohibitive to update gas monitoring devices in the field. In addition, typical gas monitoring devices do not allow for individual electronic components to be updated. As a result, industrial users often do not obtain updated systems until they purchase a new gas monitoring device, which may take many years to occur. Accordingly, industrial users and workers would benefit from a system that allows for system-critical components of a gas monitoring device to be replaced and/or updated efficiently and cost-effectively without requiring the replacement of the entire gas monitoring device or the purchase of multiple pieces of equipment.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a gas monitoring system may include a module having a mobile form factor. The module may include a memory configured to store a firmware application and data, a processor operably coupled to the memory and configured to execute firmware to control the gas monitoring system, and at least one sensor. The gas monitoring system may include a base having at least one power source and at least one base interface. In one aspect, the gas monitoring system may include at least one module interface arranged within the base and configured to interface with the at least one base interface, thereby operably coupling the module to the base. The module may be configured to receive power from the base and to control the base responsive to being connected to the base.

In an embodiment, a method of monitoring gas using a gas monitoring apparatus may include detecting at least one concentration of at least one gas using the gas monitoring apparatus. The gas monitoring apparatus may include a module having a mobile form factor. The module may include a memory configured to store a firmware application and data, a processor operably coupled to the memory and configured to execute firmware to control the gas monitoring apparatus, and at least one sensor. The gas monitoring apparatus may include a base having at least one power source and at least one base interface. In one aspect, the gas monitoring apparatus may include at least one module interface arranged within the base and configured to interface with the at least one base interface, thereby operably coupling the module to the base. The module may be configured to receive power from the base and to control the base responsive to being connected to the base. In one aspect, the method may include generating at least one alarm configured to alert a user to a hazardous condition based on the at least one concentration of the at least one gas.

BRIEF DESCRIPTION OF THE DRAWINGS

The above and other objects of the present invention will become more readily apparent from the following detailed description taken in connection with the accompanying drawings.

DETAILED DESCRIPTION

The described technology generally relates to a gas monitoring system (the "system") that includes a base component (the "base") and a separate module component (the "module"). The module may be configured to be operably coupled to the base component through corresponding interface connectors. In some embodiments, the module may also be configured to be operably coupled to a docking station and/or a data transfer device through corresponding interface connectors to connect the module to the docking station and/or the data transfer device. In some embodiments, the module may be connected to the docking station and/or the data transfer device through a cradle. In some embodiments, the module may also be coupled wirelessly and/or through wired connections to other modules, to other system elements, and/or to external elements.

In some embodiments, the system may be fully functional, for example, to monitor for gases and generate alarms relating thereto, when the module is connected to the base. In some embodiments, the base may have limited or no functionality when disconnected from the module. For example, the base may be configured to provide display and alarm testing functions when disconnected from the module. In some embodiments, the module may have limited functionality when disconnected from the base. For instance, the module may be configured to provide gas detection, bump and calibration functions, and to communicate with a docking station and/or computing devices when disconnected from the base. In some embodiments, the base may perform all or some of the functions described herein (for instance, have "full functionality") when disconnected from the module. In some embodiments, the module may perform all or some of the functions described herein (for instance, have full functionality) when disconnected from the base.

In some embodiments, the module may be configured to include components that typically have an increased potential for upgrades, replacement, maintenance, or other modifications ("high maintenance components") compared with components within the base. For example, high maintenance components may include gas sensors and firmware. Alarms, displays, or the like may typically have a lower rate of being upgraded, replaced, or requiring maintenance ("low maintenance components") than other system components, for example, in comparison to high maintenance components. In some embodiments, the low maintenance components may be arranged within the base. The module may be configured as a smaller and more portable component as compared to the base, which may generally be larger and heavier than the module. In some embodiments, the module may have a mobile or ultra-mobile form factor that is configured to facilitate portability, for example, by being able to be easily carried by a user. In some embodiments, the base may have a stationary or substantially stationary form factor. For example, the base may be and/or may be installed within a stationary or substantially stationary object or structure, such as a wall, a vehicle, mining equipment, or the like. In this manner, high maintenance components may be arranged in a module that has a smaller and more portable form factor than the base or the system overall. For example, if new or updated components of the module are available, the module may be disconnected from the base in the field, transported to a location where the module may be updated, and then transported back to the field and connected to the base. In another example, if new or updated components of the module are available, the module may be disconnected from the base and the entire module replaced with a new module having the new or updated components. As such, industrial users may obtain an upgraded system without having to replace the entire system or transport the entire system to a different location. In addition, gas detection and processing functions, which are typically performed by high maintenance components, in the module may be separated from comparatively lower-level functions, which are typically low maintenance components, such as display and alarm functions, in the base.

In some embodiments, the base may be configured to operate with different types of modules, for example, having different gas sensors, firmware, or the like. In this manner, a single base station may be used to provide different systems and/or functions depending on the type of module connected to the base station.

Accordingly, systems configured according to some embodiments may allow industrial users and system manufacturers to easily, efficiently, and cost-effectively upgrade their systems and use a wider range of gas detection and processing functions with a single base in the field than is available using conventional gas detection technology.

Figure 1:
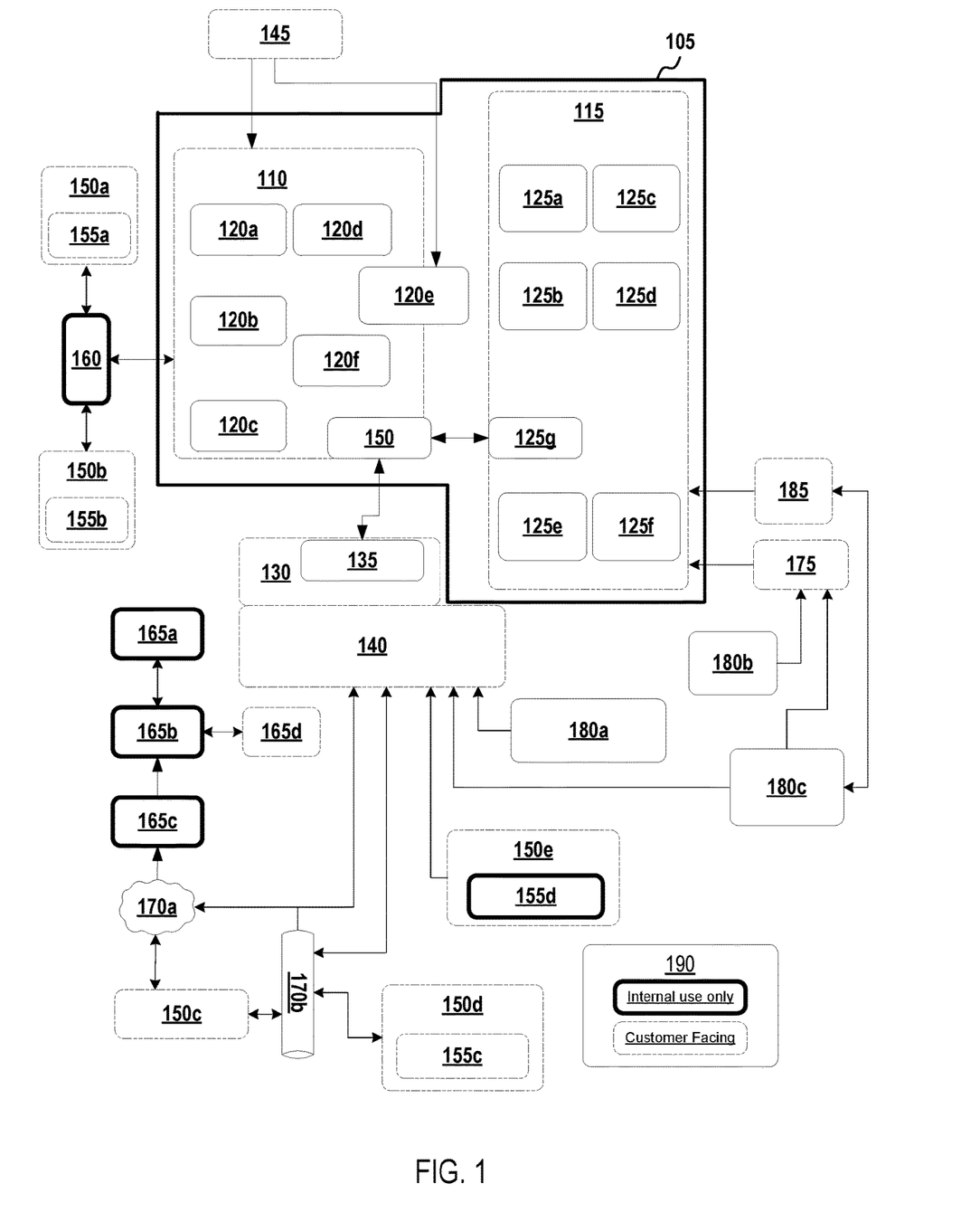
FIG. 1 depicts an illustrative gas monitoring system according to some embodiments.

FIG. 1 depicts a gas monitoring system according to some embodiments. As shown in FIG. 1, a system 105 may include a module 110 and a base 115. The module 110 may include various components, such as a battery 120a, data logs 120b (for example, data for bump tests, calibrations, measurement data, datalog data, diagnostics, errors, alarm events, instrument settings, sensor settings, or the like), communication transceivers 120c (for example, wireless communication transceivers), gas sensors 120d, a pump 120e (for example, a sampling pump for aspirated operation), firmware 120f, and/or a module interface connector 150. The module 110 may also include a non-transitory memory and processing hardware for executing the firmware 120f, generating and storing the data logs 120c, controlling the functions of the system 105, and/or executing a bootloader application. Illustrative memory elements and processing hardware may include, without limitation, a CPU 505, ROM 510, RAM 515, and/or a memory device 525 (for instance, flash memory) depicted in FIG. 5. In some embodiments, the firmware 120f may be upgraded via the bootloader application over a communication protocol, such as Modbus or through wireless communications. In some embodiments, certain of the components of the gas detection system may be for internal use only or customer (or user) facing components, as indicated according to legend 190.

In some embodiments, the system 105 may be configured to operate in different modes depending on the type of module 110 that is installed in the base 115. Non-limiting types of modes may include a diffusion mode and an aspirated mode.

In some embodiments, the system 105 may be configured to communicate with other systems, for instance, through the communication transceivers 120c. The system 105 may be able to transmit and/or receive information to/from other systems including, without limitation, alert messages (for instance, alarms, gas concentrations, faults, low battery conditions, device and/or component identification, or the like) and/or ongoing status messages (for instance, "on," "working," identifiers, or the like).

The base 115 may include various components, such as a display 125a, alarms 125b, a human machine interface (HMI) 125c, warnings 125d, battery charge indicator 125e, a battery 125f, and a base interface connector 125g. The module interface connector 150 may be connected to the base interface connector 125g to operably couple the module 110 to the base 115. Non-limiting examples of alarms 125b may include, without limitation, audio and/or visual local high gas alarm, local low gas alarm, local positive over-range alarm, local negative over-range alarm, and/or a remote gas alarm. The warnings 125d may be configured to get the attention of users in the area of the system 105, such as through flashing lights or warning tones that are different than alarm tones. Non-limiting examples of warnings may include audio and/or visual low battery warning, calibration due warning, bump due warning, bump fail warning, zero fail warning, local system error warning, RAM test failure warning, flash test failure warning, sensor checksum failure warning, pump test warning, and/or instrument checksum failure warning.

In some embodiments, the module 110 may be electrically and physically connected to the base 115. In some embodiments, the module 110 and the base 115 may be configured to communicate through the interface connectors 150 and 125g. The interface connectors 150 and 125g may be configured to communicate using any communication protocol known in the art. In some embodiments, the module interface connectors 150 and 125g may be configured to communicate using a serial communications protocol, such as the Modbus communication protocol. In some embodiments, the base 115 may include an indicator (not shown) configured to indicate whether the module 110 is and/or is not connected (or properly connected) to the base 115. In some embodiments, the system 105 may only function, or may only function to monitor gases, when the module 110 is connected to the base 115. In some embodiments, the module 110 and/or the base 115 may be configured to interface with additional devices, for example, through the interface connectors 150 and 125g. In some embodiments, the additional devices may include a maintenance device, such as a calibration adapter.

In some embodiments, neither the module 110 nor the base 115 is capable of operating independently. For instance, in some embodiments, the module 110 may only operate when installed in the base 115 or the cradle 130 (i.e., for docking functions), and the base may only operate when the module is connected thereto. In such embodiments, only a complete system 105 (for instance, a system having a base 115 with a module 110 connected thereto) is capable of performing gas detection and alarm functions.

In some embodiments, the module 110 may be operably coupled to a docking station 140. In some embodiments, the module 110 may be operably coupled to the docking station 140 through a cradle 130, for instance, by connecting the module interface connector 150 to interface connector 135 of the cradle. The cradle 130 may be operably coupled to the docking station 140. In some embodiments, the docking station 140 may be configured to provide docking station functions to the module 110. In an embodiment using a cradle 130, the docking station 140 may be configured to provide the docking station functions to the module 110 through the cradle. Illustrative and non-limiting examples of docking station functions may include bump and calibration testing, reporting, information presentation via computing devices 150d, 150e in communication with the docking station, and other docking station functions as would be known to a person having ordinary skill in the art.

In some embodiments, the docking station 140 may be configured as an iNet™-compatible docking station as provided by Industrial Scientific Corporation of Pittsburgh, Pa., United States. In some embodiments, the docking station 140 may be configured as a DS2 Docking Station™ provided by Industrial Scientific Corporation. The docking station 140 may be in communication with various networks, such as the Internet 170a and/or an Ethernet network 170b. Through the networks 170a, 170b, the docking station 140 may be in communication with various management systems and/or software, including, without limitation, DSX™ Docking Station servers 150c and software 155c and iNet™ administrative consoles 165a, databases 165b, servers 165c, and control systems 165d.

The module 110 may be in communication with various computing devices 150a, 150b, for example, through communication transceiver 120e. The module 110 may communicate with the computing devices 150a, 150b using various communication protocols and/or software as would be known to a person having ordinary skill in the art. In some embodiments, the module 110 may communicate with the computing devices 150a, 150b using Device Upgrading Service Software (DUSS) and/or Accessory Software (AccSW) as provided by Industrial Scientific Corporation for, among other things, upgrading the firmware 120f of the module. Calibration and/or bump testing of the module 110 may be performed using various calibration and/or bump testing devices 145, for example, in addition to any calibration and/or bump testing functionality provided through the docking station 140.

The system 105 may use various power sources to power the system and/or charge the batteries 120a, 125f of the components, such as a charging cable 180a (for example, DC to DC, 12V, or the like), inlet power 180b (for example, DC to DC, 12V, or the like), and/or inlet power 180c (for example, AC to DC, 100-240V, or the like) through various charging accessories 175 and/or field deployable, intrinsically safe power supplies 185. In some embodiments, at least one of the power sources may be arranged within the base 115. In some embodiments, at least one of the power sources may be arranged within the module 115. In some embodiments, the module 110 may be configured to receive power from the base 115. In some embodiments, the module 110 may not include a power source and may receive power to operate from power sources arranged within the base 115.

The gas sensors 120d may include any gas sensors known in the art. Non-limiting examples of sensors 120d may include catalytic sensors, electrochemical sensors, infrared (IR) sensors, and photo-ionization detection (PID) sensors.

In some embodiments, the module 110 may include one gas sensor 120d. In some embodiments, the module 110 may include a plurality of gas sensors 120d. In some embodiments, the module 110 may include 1 gas sensor 120d, 2 gas sensors, 3 gas sensors, 4 gas sensors, 5 gas sensors, 10 gas sensors, 15 gas sensors, 20 gas sensors, 50 gas sensors, 100 gas sensors, 1000 gas sensors, 1-3 gas sensors, 1-5 gas sensors, 1-10 gas sensors, 1-100 gas sensors, 1-1000 gas sensors, and any value or range between any two of these values (including endpoints). Although non-limiting examples of the number of gas sensors 120d are provided herein, embodiments are not so limited, as the module 110 may include any number of gas sensors capable of operating according to some embodiments.

In some embodiments, the module 110 may not include a gas sensor 120e. In some embodiments, the module 110 may be configured to operate as a wireless receiving station with or without gas sensors 120d. In some embodiments, the module 110 (and/or one or more other portions of the system 105) may include non-gas sensors (not shown). Illustrative and non-restrictive examples of non-gas sensors may include radiation sensors, weather sensors, accelerometers, light sensors, motion sensors, video sensors, tactile sensors, or any other type of sensor known in the art.

In some embodiments including a plurality of gas sensors 120d, portions of the gas sensors may be configured to detect and/or measure different types of gas. Non-limiting types of gas that may be detected by the gas sensors 120d may include oxygen, lower explosive limit (LEL) of flammable gases and vapors, carbon monoxide, hydrogen sulfide, carbon monoxide and hydrogen sulfide (COSH), ammonia, nitrogen dioxide, sulfur dioxide, volatile organic compounds (VOC), carbon dioxide, carbon monoxide with low hydrogen, chlorine, hydrogen, hydrogen cyanide, combustible gases, methane, hydrogen chloride, nitric oxide, phosphine, and combinations thereof. The gas sensors 120*d* may be arranged in various configurations on and within the module 110. For instance, a plurality of gas sensors 120*d* may be arranged on multiple surfaces and/or planes of the module 110. In some embodiments, at least a portion of the gas sensors 120*d* may include redundant sensors, for example, such as sensors using DualSense™ sensor technology provided by Industrial Scientific Corporation.

Figure 2:
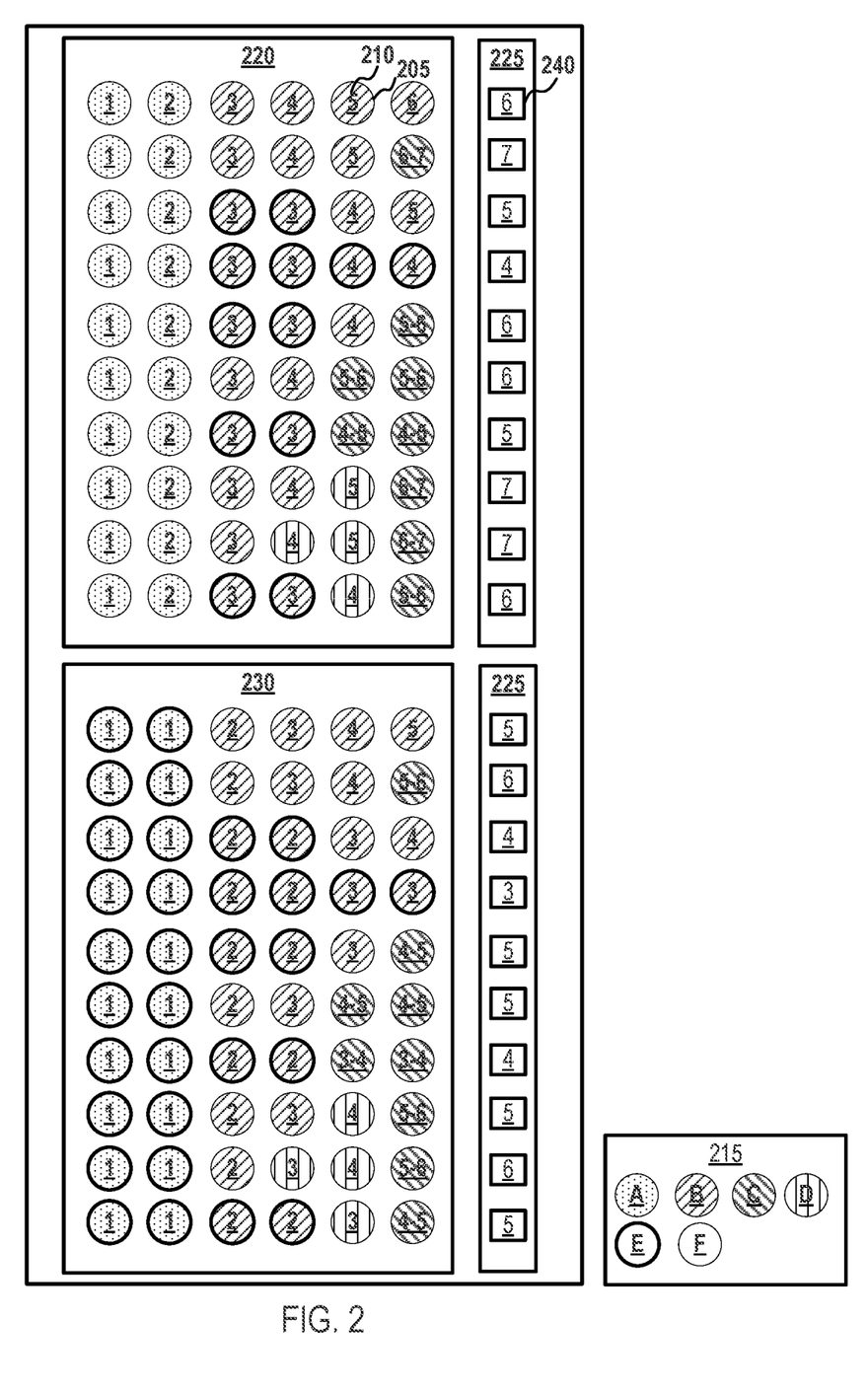
FIG. 2 depicts an illustrative gas sensor configuration of a gas monitoring system according to some embodiments.

FIG. 2 depicts an illustrative gas sensor configuration for a module having 6 sensor positions according to some embodiments. As shown in FIG. 2, a plurality of sensors 205 associated with sensor numbers 210 may be arranged on or within a module. The sensor configuration of a module may include low power sensor configurations 220 and/or high and low power sensor configurations 230. Readings 240 for the sensors may be presented on a display 225 on the base. The legend 215 provides the shading and/or outline properties to indicate various types of sensors 205. Non-limiting examples of sensors may include high power sensors (for instance, catalytic bead sensors, infrared sensors, or photoionization detectors) A, low power sensors (for instance, electrochemical sensors or low power infrared sensors) B/D, dual gas sensors (for instance, carbon monoxide/hydrogen sulfide sensors) C, redundant sensors E (for instance, DualSense™ sensors), and non-redundant (or "single") sensors F.

Figure 3:
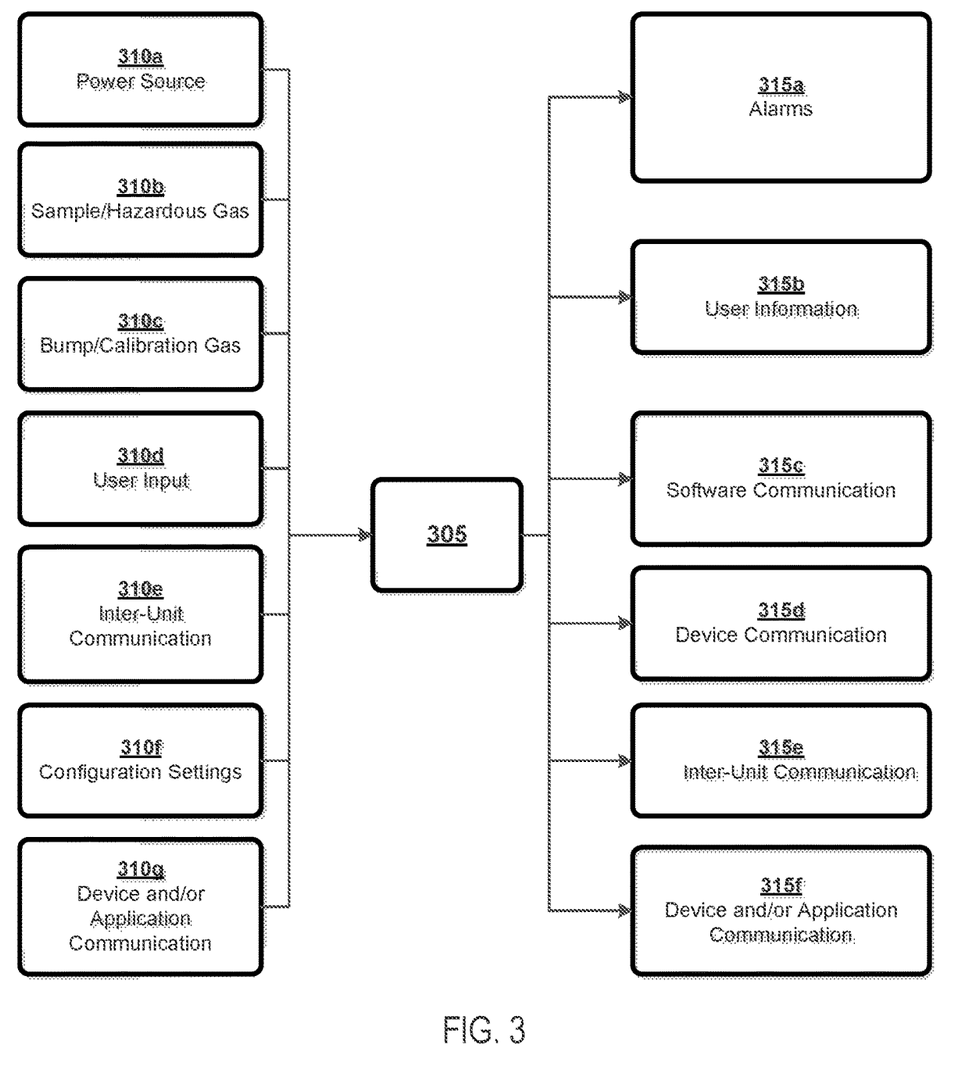
FIG. 3 depicts illustrative inputs and outputs for a gas monitoring system according to some embodiments.

FIG. 3 depicts illustrative inputs and outputs for a gas monitoring system according to some embodiments. As shown in FIG. 3, a system 305 may receive various inputs 310*a-g* and provide various outputs 315*a-f*. Illustrative inputs may include, without limitation, power source inputs 310*a* (including, for instance, temporary and continuous power source inputs), sample and/or hazardous gas input 310*b* that may be analyzed by the system 305, bump and/or calibration gas input 310*c* to test and/or calibrate the system, user input 310*d* for controlling the system or accessing system information (for instance, unit on/off, screen selection, configuration, or the like), inter-unit communication 310*e* between different systems (for instance, alarm or status messages), configuration settings 310*f*, and device and/or application communication input 310*g*, for example, for communicating to external computing devices and/or applications.

Non-limiting examples of outputs generated by the system 305 may include alarms 315*a* (for example, audio, visual, confidence signals, low battery, system error, or the like), user information 315*b* (for example, sensor types, system status, sensor replacement, battery state, calibration needed, last calibration date, and/or exposure data), software communication 315*c* (for example, communication to software for configuration, maintenance and service, reporting, or the like, such as iNet™, DUSS, AccSW, and/or manufacturer applications), device communication 315*d* (For example, alarm relay messages), communication 315*e* to other systems, and outgoing device and/or application communications 315*f* (for example, device logs, status, alarms, or the like). The alarms 315*a* may be configured as audio and/or visual alarms for communicating the current status of the system 305 to the immediately surrounding area, other systems, and/or external computing devices or applications.

Figure 4A:
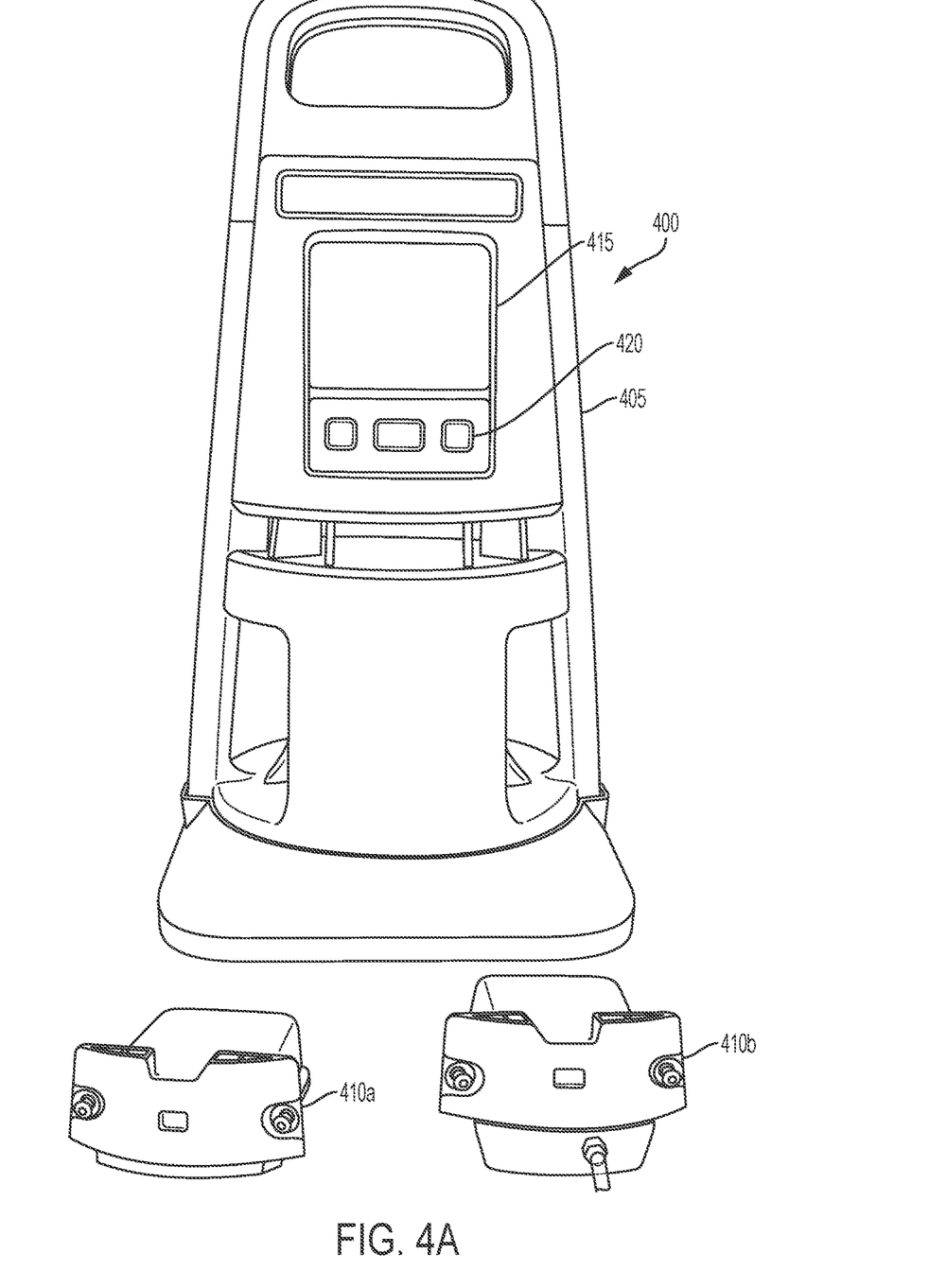
FIG. 4A depicts a front view of an illustrative gas monitoring system according to a first embodiment.
Figure 4B:
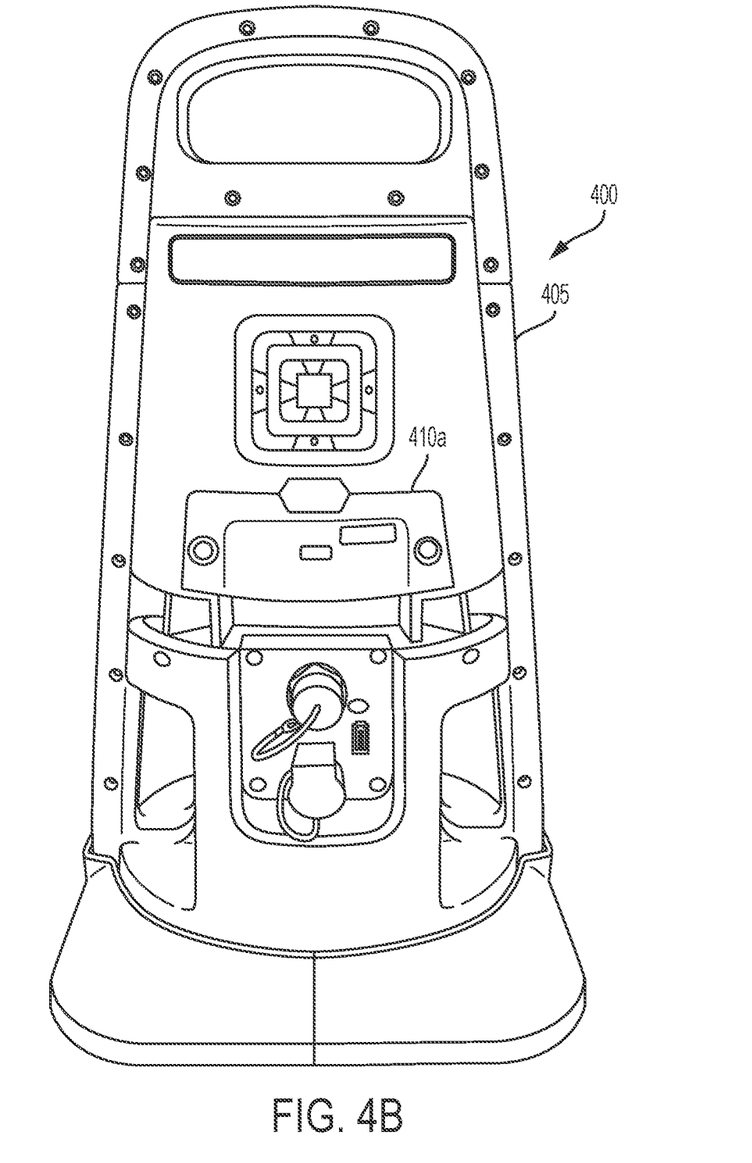
FIG. 4B depicts a back view of an illustrative gas monitoring system according to a first embodiment.
Figure 4C:
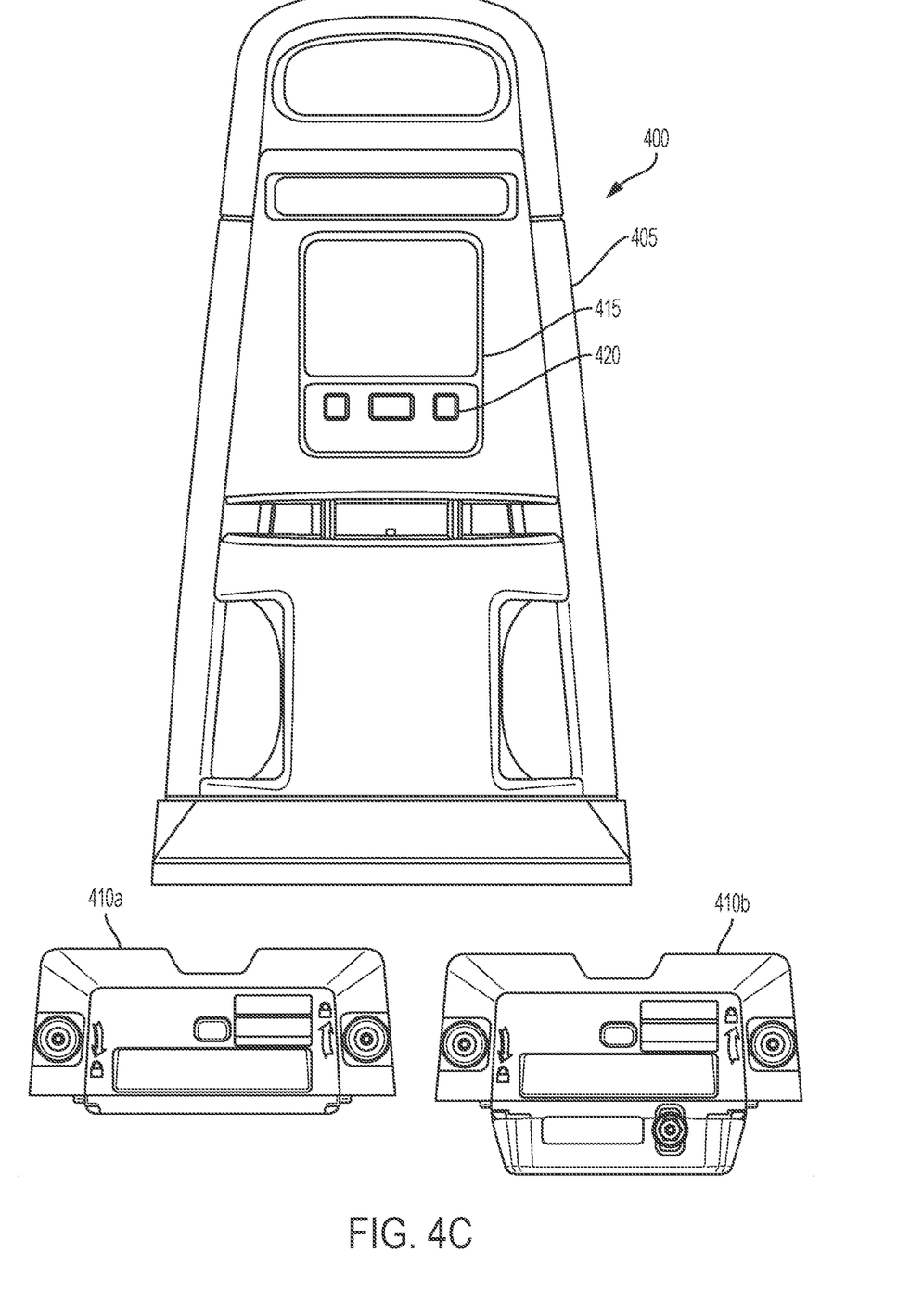
FIG. 4C depicts a front view of an illustrative gas monitoring system according to a second embodiment.
Figure 4D:
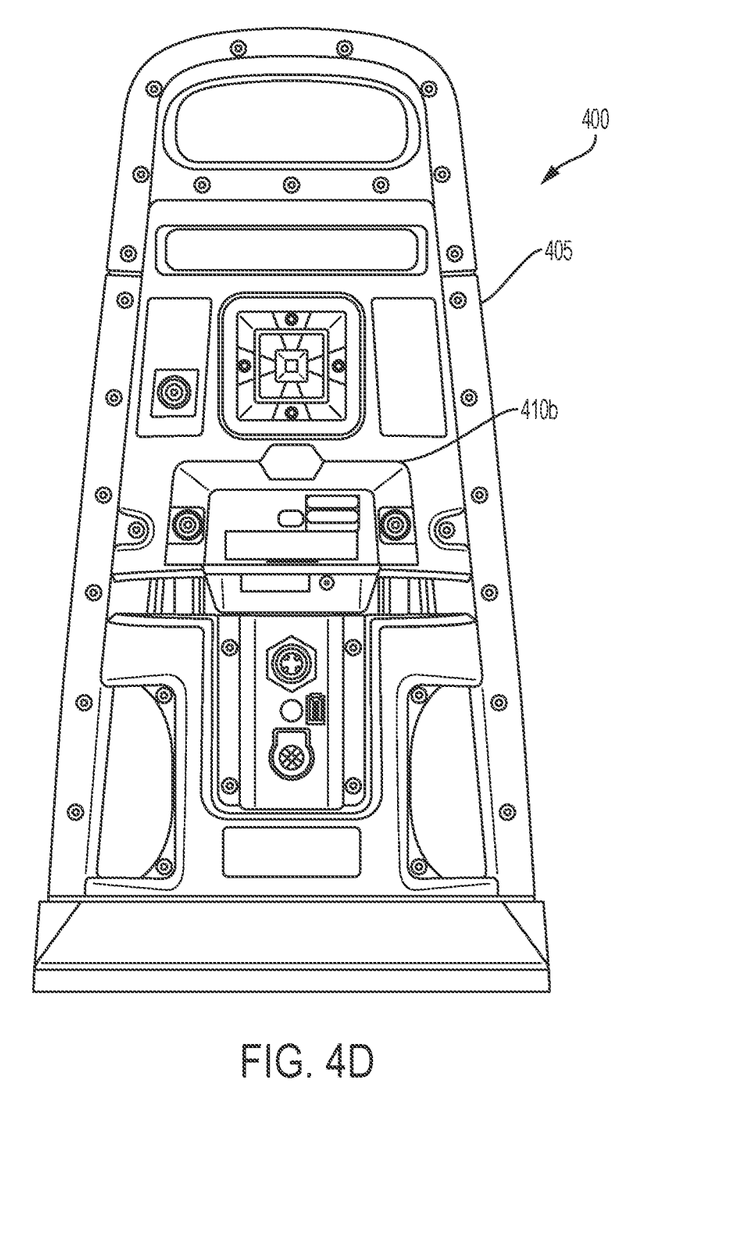
FIG. 4D depicts a back view of an illustrative gas monitoring system according to a second embodiment.

FIG. 4A depicts an image of a front view of an illustrative gas monitoring system according to a first embodiment and FIG. 4C depicts a graphical representation of a front view of an illustrative gas monitoring system according to a second embodiment. As shown in FIGS. 4A and 4C, a system 400 may include a base 405 and modules 410*a*, 410*b*. In some embodiments, the system 400 may use a plurality of modules 410*a*, 410*b*. In some embodiments, the system 400 may use one module 410*a*, 410*b*. FIGS. 4A and 4C depict a diffusion module 410*a* and an aspirated module 410*b*. The base includes a display 415 and buttons 420 configured to initiate certain system functions. Non-limiting examples of buttons 420 may include a power on/off button and a user interface access button. FIG. 4B depicts an image of a back view of an illustrative gas monitoring system according to a first embodiment and FIG. 4D depicts a graphical representation of a back view of an illustrative gas monitoring system according to a second embodiment. As shown in FIGS. 4B and 4D, in some embodiments, a module 410*a* or 410*b*, respectively, may be installed in the base 405 to form a complete system 400. As shown in FIGS. 4A-4D, the gas monitoring system and/or components thereof may have a shape generally resembling a safety cone. For instance, the base 405 may have a shape generally resembling a safety cone.

Figure 5:
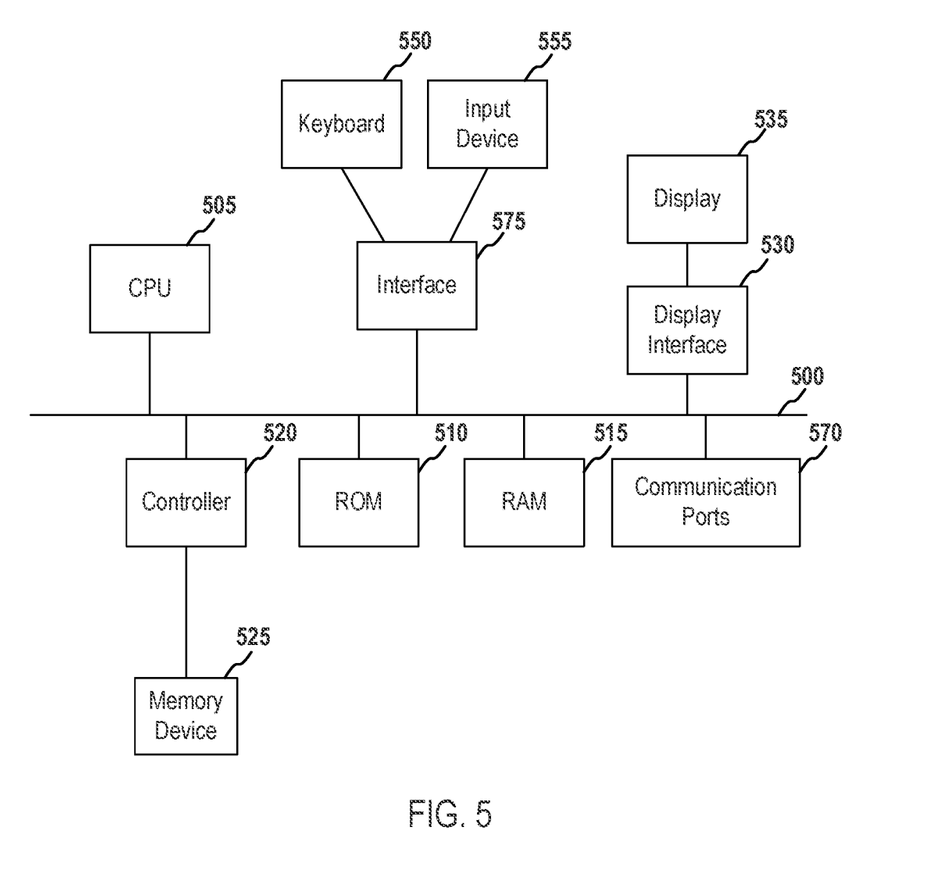
FIG. 5 illustrates various embodiments of a computing device for implementing the various methods and processes described herein.

FIG. 5 depicts a block diagram of exemplary internal hardware that may be used to contain or implement the various computer processes and systems as discussed above, for example, as a processing circuit for module 110. A bus 500 serves as the main information highway interconnecting the other illustrated components of the hardware. CPU 505 is the central processing unit of the system, performing calculations and logic operations required to execute a program. CPU 505, alone or in conjunction with one or more of the other elements disclosed in FIG. 5, is an exemplary processing device, computing device or processor as such terms are used within this disclosure. Read only memory (ROM) 510 and random access memory (RAM) 515 constitute exemplary memory devices.

A controller 520 interfaces with one or more optional memory devices 525 to the system bus 500. These memory devices 525 may include, for example, an external or internal DVD drive, a CD ROM drive, a hard drive, flash memory, a USB drive and/or the like. As indicated previously, these various drives and controllers are optional devices. Additionally, the memory devices 525 may be configured to include individual files for storing any software modules or instructions, auxiliary data, common files for storing groups of results or auxiliary, or one or more databases for storing the result information, auxiliary data, and related information as discussed above.

Program instructions, software or interactive modules for performing any of the functional steps as described above may be stored in the ROM 510 and/or the RAM 515. Optionally, the program instructions may be stored on a tangible computer-readable medium such as a compact disk, a digital disk, flash memory, a memory card, a USB drive, an optical disc storage medium, such as a Blu-ray™ disc, and/or other recording medium.

An optional display interface 530 may permit information from the bus 500 to be displayed on the display 535 in audio, visual, graphic or alphanumeric format. Communication with external devices may occur using various communication ports 570. An exemplary communication port 570 may be attached to a communications network, such as the Internet or a local area network.

The hardware may also include an interface 575 which allows for receipt of data from input devices such as a keyboard 550 or other input device 555 such as a mouse, a joystick, a touch screen, a remote control, a pointing device, a video input device and/or an audio input device.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A monitoring device comprising:
  a module, comprising:
    a memory configured to store a firmware application and data,
    a processor operably coupled to the memory and configured to execute the firmware application to control the monitoring device,
    a wireless communication transceiver, wherein the wireless communication transceiver is configured to allow inter-unit communications between the module and another monitoring device external to the monitoring device, wherein the inter-unit communications relate to a status of the module or the other monitoring device or an alarm condition of the module or the other monitoring device,
    at least one sensor, and
    a module housing including a module interface connector; and
  a base comprising a base housing including a base interface connector structured to receive the module interface connector, wherein the module is structured to communicate with the base by way of the module interface connector and the base interface connector, wherein the module is structured to be installed in the base, wherein the monitoring device that includes the module and base is operable to monitor data measured via the at least one sensor and provide monitoring and alarm functions when the module is physically connected to the base, and wherein neither the base nor the module is capable of operating independently to provide the monitoring and alarm functions when disconnected from one another, wherein the module is replaceable separately from the base.

2. The monitoring device of claim 1, wherein the at least one sensor comprises at least one of a gas sensor, a radiation sensor, a weather sensor, an ambient environment sensor, a sound pressure wave sensor, or a motion sensor.

3. The monitoring device of claim 1, wherein the module is configured to transmit and receive at least one of alert messages or status messages from other modules external to the monitoring device via the wireless communication transceiver.

4. The monitoring device of claim 1, wherein the monitoring device that includes the module and the base is a gas monitoring device and is configured to operate in at least one of a diffusion mode or an aspirated mode depending on a type of the module coupled to the base.

5. The monitoring device of claim 1, wherein the module is configured to interface with at least one maintenance device when disconnected from the base, the at least one maintenance device comprising at least one of a docking station or a data transfer device.

6. The monitoring device of claim 1, wherein the at least one sensor comprises a gas sensor, and wherein the monitoring device that includes the module and the base is a gas monitoring device and is operable to monitor gas measured via the gas sensor.

7. The monitoring device of claim 1, wherein the module is configured to interface with at least one of a bump device or a calibration device.

8. The monitoring device of claim 1, wherein the base includes a battery structured to provide power to the module by way of the base interface connector.

9. The monitoring device of claim 1, wherein the base is structured to output an audio or visual representation of the status of the module or the other monitoring device.

10. The monitoring device of claim 8, wherein the module does not include a power source within the module housing, and the module is structured to receive the power from the base via the base interface connector.

11. The monitoring device of claim 1, wherein the base has a shape generally resembling a safety cone, and the module is physically smaller and lighter than the base.

12. The monitoring device of claim 1, wherein the memory, the processor, and the wireless communication transceiver are within the module housing, and the at least one sensor is on or within the module housing.

13. The monitoring device of claim 1, wherein the module is physically installed in the base.

14. A method of monitoring gas using a first gas monitoring apparatus, the method comprising:
    detecting at least one concentration of at least one gas using the first gas monitoring apparatus, the first gas monitoring apparatus comprising:
        a module, comprising:
            a memory configured to store a firmware application and data,
            a processor operably coupled to the memory and configured to execute the firmware application to control the first gas monitoring apparatus,
            a wireless communication transceiver, wherein the wireless communication transceiver is configured to allow inter-unit communications between the module and a second gas monitoring apparatus, wherein the inter-unit communications relate to a status of the module or the second gas monitoring apparatus or an alarm condition of the module or the second gas monitoring apparatus,
            at least one gas sensor; and
            a module interface connector; and
        a base comprising a base housing including a base interface connector structured to receive the module interface connector, wherein the module is structured to communicate with the base by way of the module interface connector and the base interface connector, wherein the module is structured to be installed in the base, wherein the first gas monitoring apparatus is operable to monitor data measured via the at least one gas sensor and provide gas detection and alarm functions when the module is physically connected to the base, and wherein neither the base nor the module is capable of operating independently to provide the gas detection and alarm functions when disconnected from one another; and
    generating at least one alarm configured to alert a user to a hazardous condition based on the at least one concentration of the at least one gas when the module is connected to the base.

15. The method of claim 14, wherein the module is replaceable separately from the base.

16. The method of claim 14, further comprising, transmitting and receiving at least one of an alert message or a status message from at least one second module external to the first gas monitoring apparatus via the wireless communication transceiver arranged within the module of the first gas monitoring apparatus.

17. The method of claim 16, wherein the first gas monitoring apparatus is configured to operate in at least one of a diffusion mode or an aspirated mode depending on a type of the module coupled to the base.

* * * * *